United States Patent
Katzen

(10) Patent No.: US 7,208,160 B2
(45) Date of Patent: Apr. 24, 2007

(54) PROCESS OF TREATING SEA ALGAE AND HALOPHYTIC PLANTS

(76) Inventor: Sol Katzen, 62 Hanassi Street, Herzliya Pituach (IL) 46399

( * ) Notice: Subject to any disclaimer, the term of this patent is extended or adjusted under 35 U.S.C. 154(b) by 529 days.

(21) Appl. No.: 10/647,305

(22) Filed: Aug. 26, 2003

(65) Prior Publication Data

US 2005/0048080 A1    Mar. 3, 2005

(51) Int. Cl.
*A61K 36/02*    (2006.01)
*A61K 9/00*     (2006.01)
*A61K 47/00*    (2006.01)

(52) U.S. Cl. .................. 424/195.17; 424/400; 424/439

(58) Field of Classification Search .................... 435/6; 424/195.17, 400, 439
See application file for complete search history.

(56) References Cited

U.S. PATENT DOCUMENTS

| 4,369,199 A | 1/1983 | Katzen |
| 4,986,985 A | 1/1991 | Grossman et al. |
| 5,648,313 A | 7/1997 | Pohl |

OTHER PUBLICATIONS

DW 2002-563565, filed Feb. 2002, Derwent KR, Park et al.*
Encyclopedia Britannica, Macropedia, vol. I, (1974), p. 489.
Encyclopedia Britannica, Macropedia, vol. I, (1974), p. 89.
Agar, Oregon State University, (food.oregonstate.edu/gums.agar.html), (Aug. 8, 2003 AOL), update Jul. 14, 2003.
Encyclopedia Britannica, Micropaedia, vol. V, (1974), p. 426.
What Is Carrageenan?, Tacara, (www.tacara.com.my/articles/carrageenan %20article1), (Aug. 8, 2003 AOL).
AisonChem, (www.aisonschem.com.cn/carrageenan), (Aug. 8, 2003 AOL), copyright 2003.
Schenck, K., Wound dressings (1): Calcium alginates for moist wound treatment, WundForum Wound Care, (Aug. 10, 2003 AOL).
Jork, A., et al., Appl. Microbiol. Biotechnol., (2000), 53: 224-229.
Marinalg Welcome, (www.marinalg.org/products/algina_int), (Aug. 8, 2003 AOL).
Truus, Kalle, et al., Proc. Estonian Acad. Sci. Chem., (2001), 50, 2, 95-103.
Training Manual On Gracilaria Culture and Seaweed Processing In China, Chapter III (Cont.), 3) Algin, (www.fao.org/docrep/field/003/AB730E/AB730E04), (Aug. 10, 2003 AOL).
Flora Celtica, A Brief History of Scottish Seaweed Use, (193.62.154.38/celtica/history.htm), (Aug. 10, 2003 AOL).
Wikipedia, Agar, (www.wikipedia.org/wiki/Agar), (Aug. 8, 2003).
Agar, substance obtained from seaweed, The Columbia Encyclopedia, 6th Ed., (2001), (www.bartleby.com/65/ag/agar), (Aug. 8, 2003 AOL).
Sea Algae, (library.thinkquest.org/JO02608/sea_algae.htm), (Aug. 7, 2003 AOL).
Marine Plants, Algae Lecture, (darter.ocps.net/classroom/klenk/algae.htm), (Aug. 7, 2003 AOL).
NII-REO, Journal of Applied Phycology, 11(6), p. 493-502, 1999, abstract, (reo.nii.ac.jp/journal/HtmlIndicate/contents/SUP00000/000/JOU0001000266/ISSO . . .), (Aug. 10, 2003 AOL), cop.
Saude, N., et al., Process Biochemistry 38 (2002) 273-278.
Seaweed's Nutritional Value, Fisheries Information Newsletter #95 (Oct.-Dec. 2000), www.spc.int/coastfish/News/Fish_news/95/NIAR_9), (Aug. 10, 2003 AOL).
Maneveldt, Gavin W., et al., Of dead man's fingers, cord weed and hanging wrack: . . . (www.botany.uwc.ac.za/gavin/Pop_articles/Popart10), (Aug. 10, 2003 AOL).
Phycocolloid, (www.botany.uwc.ac.za/algae/StudentAssignments/dalenorman98/types), (Aug. 10, 2003 AOL).
Tidal Salt Marshes, (ag.arizona.edu/azaqua/aquaplants/notes/MARSHES.HTM), (Aug. 4, 2003).
Wikipedia, Halophyte, (www.wikipedia.org/wiki/Halophytes), (Aug. 4, 2003 AOL).
Halophytes and Xerohalophytes, (www.botgard.ucla.edu/html/botanyTextbooks/lifeforms/halophytes/), (Aug. 4, 2003 AOL).
Halophyte DataBase, Salt-Tolerant Plants & Their Use, (www.ussl.ars.usda.gov/pls/caliche/halophyte.preface), (Aug. 7, 2003 AOL).
Alginate, Algin, Food Resource, (food.oregonstate.edu/gums/alginates.html), (Aug. 10, 2003).
What are Halophytes?, (www.usf.uni-osnabrueck.de/projects/expo2000/english/descript/descript) (Aug. 7, 2003 AOL).
Training Manual On Gracilaria Culture and Seaweed Processing In Chinga, 1) Agar, (www.fao.org/docrep/field.003/AB730E/AB730E03), (Aug. 8, 2003 AOL).

* cited by examiner

*Primary Examiner*—Christopher R Tate
*Assistant Examiner*—Randall Winston
(74) *Attorney, Agent, or Firm*—Fisher, Christen & Sabol

(57) ABSTRACT

The process of treating sea algae/halophytes. The sea algae/halophyte in an aqueous solution containing an acid is soaked for a sufficient length of time to substantially reduce the mineral content of the sea algae/halophyte. The initial mineral content is expressed on the basis of the total ash content of the untreated sea algae/halophyte in the dried state. The soak-treated sea algae is separated from the aqueous solution. The separated sea algae/halophyte can be dried to provide a dried sea algae/halophyte product having substantially reduced mineral content and increased nutritional value.

20 Claims, No Drawings

PROCESS OF TREATING SEA ALGAE AND HALOPHYTIC PLANTS

BACKGROUND OF THE INVENTION

1. Field of the Invention

The invention relates to a process for lowering the mineral (ash) content and increasing the nutritional value of sea algae and halophytes, to the product produced by such process, and to use such product as or in feed or food.

2. Background

There is little food value in the complex nitrogenous and carbohydrate compounds found in algae because humans' digestive system cannot break down these complex structures into useful metabolites during digestion. Algae do have value as roughage, however. The mineral, vitamin, and iodine content of algae provide valuable nutrients. [Encyclopedia Britannica, Macropaedia, Vol. 1, (1974), page 489] Palatable and digestible types of sea algae as food sources for humans would be desirable. Seaweeds, usually in meal form from drying and grinding, are eaten in relatively small amounts by some domesticated commercial animals as part of their diet as seaweeds do not provide the animals with a balanced diet. It seems that digestibility in animals depends upon the sea algae source and the health of the animals. The principal seaweeds consumed by animals are rockweed (*Fucus* and *Ascophyllum*) and *Laminaria* species are also used.

Dulse (texture of this rubber) is commonly dried and eaten by North Atlantic fishermen, and also eaten with fish and butter, boiled with milk and rye flour, or as a relish. Sea lettuce is sometimes used in soups. Laver, especially *Porphyra tenera*, is used in a variety of foods.

Although this invention deals only with the extraction of mineral matter from algae and halophytic plants and does not involve the extraction of various alginates, agar or carrageenans, the following references are cited inasmuch they refer to processes involving sea algae.

In essence, agar is a polymer of carbohydrate prepared from certain sea algae, e.g., some species of red algae or seaweeds. Agar is often used as a vegetarian gelatin substitutes (e.g., in soups, sauces, jellies and ice cream). It also finds use in icings, glazes, cookies, meringues, confectionery, pie fillings, piping gels, canned meat and fish.

Agar is extracted from various varieties of red algae, principally from species of *Gelidium, Gracilaria, Pterocladia, Acanthopeltis* and *Ahnfeltia*. The first two are sea weeds. Agar is extracted from sea algae by means of hot water. [Encyclopedia Britannica, ibid., page 89] In more detail, agar (or agar-agar) is prepared by boiling, purifying and drying sea algae to an amorphous and translucent product (usually put into a powder, flake or brick form). [Encyclopedia Britannica, ibid.] Agar is extracted from red algae and then purified. [Agar, Oregon State University, (http://food.oregonstate.edu/gums.agar.html), (Aug. 08, 2003 AOL), Update Jul. 14, 2003, two pages]

Carrageenans are naturally occurring linear sulfated polysaccharides which occur in certain species of red seaweed (Rhodophycae) of the Solieriaceae, Gigartinaceae, Furcellariaceae, Phyllophoraceae, Hypneaceae, Rhabdoniaceae, and Rhodophyllidaceae families. Carrageenan is extracted from various species of red algae. Carrageenan extract is removed from Irish moss by boiling dried Irish moss. [Encyclopaedia Britannica, Micropaedia, Vol. V, (1974), page 426] What Is Carrageenan?, Tacara, (http://www.tacara.com.my/articles/carrageenan%20article1.htm), (Aug. 08, 2003 AOL), four pages, states:

"The main carrageenan types, lambda, kappa and iota, can be prepared in pure form by selective extraction techniques."

"In 1884, the first successful extraction of carrageenan from *Chondrus crispus* was attributed to Schmidt, followed by a patentable process of extraction by alcohol precipitation. The production of carrageenan is a straightforward operation consisting of extraction, purification and isolation. The seaweed should be cleaned to remove any sand before extraction proceeds. Alkaline conditions are necessary to modify the galactan structure, resulting in better gelling ability. Modifications as well as differences in extraction techniques exist. Three processes are most commonly used: alcohol precipitation, freeze-thawing and gel press."

"What is semi-refined/Philippines Natural Grade (PNG) carrageenan?"

"This form of carrogeenan evolved into a food ingredient from a past that began as a way of treating raw *Eucheuma* seaweed in the Philippines prior to export . . . developed in the Philippines a pre-treatment process for the raw seaweed which yielded the item of commerce now called 'alkali treated cottonii chips'. A powder made from these chips was developed in the early 1970s for use by manufacturers of canned pet food. The performance properties of the alkali modified flour approached those of refined carrageenan . . . "

"The PNG process parallels the refined carrageenan process, except for the extraction step. In making refined carrageenan, the polysaccharide is extracted or dissolved from the seaweed to yield a carrageenan solution at a concentration of about two weight percent. PNG uses a reverse extraction process where impurities are extracted from the seaweed, and the polysaccharide is left in a gel state containing about 45 weight percent carrageenan and algal cellulose. PNG differs from refined carrageenan primarily in its relatively high algal cellulose content and lower salt content." [Pages 2 and 3]

The article makes no mention of the use of an acid. On the contrary, the article mentions the necessity of maintaining basic conditions for its purposes.

AisonsChem, (http://www.aisonschem.com.cn/carrageenan.htm), (Aug. 08, 2003 AOL), eleven pages, (Copyright 2003), states:

"Carrageenan is extracted from the raw material with water at high temperatures. The liquid extract is purified by centrifugation and/or filtration. The liquid extract may be converted into a powder by simple evaporation of water to yield the so called drum dry carrageenan."[Page 2]

Algin, broadly, are various colloidal substances extracted from brown marine algae. Algin is commercially obtained from *Fucus, Ascophyllum nodossum, Laminaria* and *Macrocystis*. Algin is obtained by digesting seaweed [sea algae] in alkali and precipitating either the calcium salt or alginic acid.

Algin herein refers specifically to soluble sodium alginate. However, algin, in a broader sense refers to alginic acid or salts of alginic acid—one has to look at the context to ascertain which meaning is being used.

Schenck, K., Wound dressings (1): Calcium alginates for moist wound treatment, WundForum Wound Care, (Aug. 10, 2003 AOL), seven pages, states:

"The manufacturing process of alginates involves crushing and washing of the raw material and dissolution of the extracted sodium alginate in water. A viscous solution is obtained which is extruded into a calcium chloride bath. hence, the sodium ions are replaced by calcium ions and the insoluble calcium alginate is precipitated." [Page 2]

Jork, A., et al. Appl. Microbiol. Biotechnol., (2000), 53:224–229, disclosed extracting alginate from the kelp *Laminaria pallida* using $Na_2CO_3$ in EDTA.

Marinalg Welcome, (http://www.marinalg.org/products/algina_inf.htm), (Aug. 08, 2003 AOL), two pages, states:

"Alginates are extracted from various species of brown seaweeds (Phaecohyceae) by a multi-step process. A typical extraction process involves first washing and treating seaweed with diluted sulfuric acid (quantitatively transforming calcium alginate into alginic acid), extraction by dissolution with alkali, separation of insolubles, then precipitation as the calcium salt, followed by acid washing to recover alginic acid. The salts and esters of alginic acids are obtained by neutralization and esterification, respectively."

Marinalg Welcome also states that algin is sometimes used in the literature for the term alginates and that alginates includes alginic acid, salts of alginic acid (sodium, potassium, ammonium, magnesium and calcium alginates) and esters (propylene glycol aginate). The e-document also states that alginates are used in a variety of human and pet foods.

Truus, Kalle, et al., Proc. Estonian Acnd. Scr. Chem., (2001), 50, 2, 95–103, states:

"In principle, the isolating process of alginates from brown algal biomass is simple, including stages of pre-extraction with hydrochloric acid (□ alginic acid), followed by washing, filtration, and neutralization with alkali (□ sodium alginate). Sodium alginate is precipitated from the solution by alcohol (isopropanol or ethanol) and usually re-precipitated (to achieve higher purity) in the same way [9]. However, the real processing scheme for alginate production is quite complicated, including 15 steps [10]." [Page 96]

"Extraction and precipitation of alginates. In all cases, alginates were isolated from the seaweeds in sodium form. Algae were processed at three principal regimes: (a) "cold" method, (b) "hot" method, and (c) modified method including extraction in boiling state.

(a) Cold method. 20 g of air-dry algae was stored (18 h) in 300 mL of 1% $CaCl_2$ solution at room temperature. After that, the seaweeds were washed with water (3×300 mL), stored (1 h) in 5% solution of hydrochloric acid, and washed again with water (3×300 mL). Then algae were treated with 3% $Na_2CO_3$ solution (100 mL, 1 h) and water (300 mL) was added to stand overnight. The viscous mixture was filtered and the sodium alginate formed was precipitated from the solution by adding isopropanol (1:4 v/v). The precipitate was filtered, washed by isopropanol, and dried in air.

(b) Hot method. The seaweeds were treated as described above (method a) with the only difference that the storing time was 3 h and the processing temperature was 50° C.

(c) Modified method. 20 g of air-dry algae was treated with boiling water (300 mL, 30 min) and with 0.5% $CaCl_2$ solution (300 mL, 100° C., 30 min). The extract was separated and the algal residues were treated with 0.5% NaCl solution (300 mL, 1 h) at 100° C. The dark-colored extract was removed and 3% $Na_2CO_3$ solution (100 mL, 100° C.) was added to the seaweeds by intensive stirring (30 min, a boiling water bath). Then, additional 100 mL of water was added and the mixture was filtered. Sodium alginate was precipitated from the solution as described above." [Page 98]

Training Manual On *Gracilaria* Culture And Seaweed Processing In China, Chapter III (Cont.), (http://www.fao.org/docrep/field/003/AB730E/AB730E04.htm), (Aug. 10, 2003 AOL), 21 pages, states:

"Pretreatment: The alginophytes (*Laminaria* sp.) are treated, first, with 0.1–0.4% commercial formallin solution at room temperature for several hours to fix the pigments together with the phenolic substances present in the thalli diminishing the coloration of the extracted liquor. Then the thalli are soaked with dilute acid such as 0.1 M $H_2SO_4$ or HCl solution for 30 minutes at room temperature to convert the metallic salts of alginate into alginic acid."

"Hot extraction: The treated wet thalli are extracted with 1% sodium carbonate solution . . . " [Page 12]

The above quotation describes the start of the manufacture of sodium alginate from sea algae by the calcification process.

There is no admission that the literature and other art described and/or quoted above and below are prior art to this application or the invention described in this application.

BROAD DESCRIPTION OF THE INVENTION

An object of the invention is to provide a process for substantially lowering the mineral (ash) content and increasing the nutritional value of sea algae and halophytes. A further object of the invention is to provide a sea algae/halophyte product that can be used in larger quantities as or in a human food or an animal fodder.

Other objects and advantages of the invention are set out herein or are obvious herefrom to one skilled in the art.

The objects and advantages of the invention are achieved by the processes and products of the invention.

As used herein, "sea algae/halophyte(s) means sea algae and/or halophytes.

The invention involves a process of treating sea algae and/or halophytes. The sea algae/halophyte is soaked in an aqueous solution containing an acid for a sufficient length of time to substantially reduce the mineral content of the sea algae/halophyte. The mineral content is expressed on the basis of the total ash content of the untreated sea algae in the dry state. The separated sea algae/halophyte can be dried. The separated sea algae/halophyte, in the wet or dried state, has substantially reduced mineral content and increased nutritional value.

The sea algae is advantageously a seaweed.

The halophyte is a salt tolerant plant such as *salicornia, suaeda, zygophyllum, atriplex*, etc. that may be cultivated or occur in nature. Halophytes occur in saline habitats along bodies of sea water, for example, coastal salt marshes, seashores, mangrove swamps and the like. These habitats are usually continuously flushed with sea water by tidal action.

The untreated sea algae/halophyte is used in the dried state or wet state. The sea algae/halophyte used in the soaking process usually has an initial total ash content of about 25 to about 40 weight percent. The soaking of the sea algae/halophyte is conducted for a minimum of three hours, advantageously for 5 to 12 hours. The soaking of the sea algae/halophyte is usually conducted at ambient temperature, preferably from 66 to 120° F. The soaking of the sea algae/halophyte is preferably conducted at ambient pressure, but can be conducted at lower or higher pressure.

In the soaking step, sufficient acid is usually present to provide a pH in the aqueous solution containing the sea algae/halophyte of less than about 5, advantageously of 2.0 to 4.0, preferably 2.5 to 3.5. Further acid can be added, as needed, to maintain the desired pH during the soaking step. The acid can be an inorganic acid, preferably hydrochloric or sulfuric acid. The acid can be an organic acid.

In the invention process, the sea algae/halophyte (dry basis) used in the soaking step has an initial total ash content of about 25 to about 40 weight percent, and the ash content of the sea algae/halophyte is reduced to about 5 to about 15 weight percent, based on the total dry weight of the acid-treated sea algae/halophyte.

The treated sea algae/halophyte is separated from the aqueous solution that contains dissolved minerals removed from the sea algae/halophyte. The separated sea algae/halophyte can be dried and reduced in size, preferably by chopping or grinding. The dissolved mineral can be separated from the aqueous solution containing the dissolved minerals by sun drying or mechanical dehydration of the aqueous solution.

The invention includes the product of the process of the invention. The sea algae/halophyte product has substantially reduced mineral (ash) content and increased nutritional value (as compared to the starting sea algae/halophyte). The sea algae prepared by the process of the invention can be used as food or feed, or as a food or feed ingredient. The invention further includes the food or feed containing the sea algae prepared by the invention process.

The invention involves a process that lowers the ash content and improves the nutritional quality of various sea algae and halophytes.

One of the limitations for the use of various sea algae, such as, kelp and other brown algae, Gracillaria and other red algae as well as enteromorpha and other green algae and halophytes is the generally high content of salt and other mineral matter. Typically, the total ash content may be in the range of 25 to 40 percent.

The carbohydrate and protein fractions in the sea algae/halophytes are diluted by this high ash content. Food and feed use of sea algae and halophytes is limited to the maximum levels of salt and other minerals tolerated by the metabolism of the various species whose diet may benefit from the inclusion of sea algae/halophyte. The purpose of the invention is to relax this constraint as well as to improve the nutritional value of the sea algae and halophytes.

The process involves soaking the wet or dried sea algae/halophytes in a dilute solution of various mineral or organic acids so that the mineral matter passes into the solution, where it can be recovered by drying or precipitation for other uses, or is discarded. The residual algae/halophyte can then be dried and ground to be used as a food or feed ingredient. The considerable vitamin-C content and natural pigmenters in the sea algae/halophyte remains. The protein and carbohydrate content is increased by the percentage of ash removed. For example, if the initial mineral content of sea algae is 40 percent and the protein content is 8.6 percent, (typical), reducing the ash content to 10 percent would leave a residual protein content of 11 to 12 percent. Other beneficial factors, such as, energy content are equally improved. The natural protein is insoluble at the operating conditions of the process and is not lost in the discarded solution.

DETAILED DESCRIPTION OF THE INVENTION

Sea water contains, among other things, dissolved inorganic substances, (minerals), dissolved organic substances and dissolved gases. Also, present are particulate matter in suspension. The concentration of the mixture of minerals in sea water is usually fairly constant but can vary in places due to evaporation and/or dilution by fresh water. The salinity of sea water in open seas generally lies between 28 to 40 parts per thousand. The dissolved minerals are present in ionic form. The mineral content, in addition to NaCl, has significant amounts of $MgSO_4$, $CaSO_4$, KCl, $MnSO4$ and bicarbonates plus minor minerals. (In standard methods, the constituents of the dissolved salts would be listed in their ionic forms.)

Any of the nontoxic sea or marine algae/halophytes can be treated by the process of the invention.

The preferred sea algae are the seaweeds that are certain red, green and brown sea (marine) algae.

Brown algae (*Phaeophyta*) that are seaweeds include kelp, gulfweed and *Fucus*. Kelp is a large seaweed. Kelp belongs to the order Laminariales (about 30 genera). Several genera of brown algae are known as kelp. *Laminaria* is a large brown seaweed. *Macrocystis* is the largest known kelp. *Nerocystis* is also a large kelp. Gulfweed is the nonscientific name for several species of the genus *Sargassum*. The species *S. natans* predominates in the Sargasso Sea. *Fucus* is a genus of brown algae and *Fucus vesiculosis* is one of its prominate species.

Red algae (*Rhodophyta*) that are seaweeds include dulse, *Gelidium*, *Chondrus* and laver. Dulse is the nonscientific name for *Rhodymenia palmata*. *Gelidium* is a genus of red algae and *G. amansil* is one of its prominate species. Irish moss is the nonscientific name for the algae species *Chondrus crispus* and sometimes for several red seaweeds associated with *Chondrus*.

The *Ulva* species of green algae (Chlorophyta) are seaweeds. The genus *Ulva* has the nonscientific name sea lettuce. *Ulva lactuca* is one of its prominent species.

The invention also applies to sea water halophytes.

The sea algae that come within the scope of the invention include those that live in seas (e.g., the Baltic Sea) that are less salty than the open sea due to the substantial fresh water influx from rivers and to geographical factors, and brackish or somewhat salty (saline) bodies of water (bays and seas, such as the Chesapeake Bay). The useful sea algae can be those from the open sea or, for example, the intertidal zones or the subtidal zone. They may be cultivated or naturally occurring.

The invention includes use of harvested and beach cast sea algae, and sea algae from algae farming. The invention further includes use of sea algae grown in artificial sea water, that is, hydrponically grown sea algae.

The sea algae/halophytes used normally has an initial total (dry) ash content of about 25 to about 40 weight percent, based on the initial total dry weight of the sea algae/halophytes. However, sea algae/halophytes having any mineral content can be used in the invention process with the result of substantially reduced mineral content and increased nutritional value.

As used herein, ash means the solid mineral residue left after the sea algae/halophyte is thoroughly burned or oxidized by chemical means. The term mineral means the inorganic substances. (Some of the inorganics may come off in gaseous form depending on the ash measurement method.)

The sea algae/halophyte used in the invention process can be in the natural state (i.e., non-dried) or the partially or totally dried state. The sea algae/halophytes can be air dried or dried by any other suitable means (such as, in mechanical dryers). If dried sea algae/halophyte is used, air drying is advantageous in the economic sense over heat drying.

The sea algae/halophyte used in the invention is not pretreated with any chemicals or stored in or with addition of any chemicals. For example, formaldehyde (solution) is not added to the sea algae/halophyte being stored before treatment in the invention process. The sea algae/halophyte is not pretreated with $CaCl_2$.

The sea algae/halophyte can be converted into smaller pieces or reduced in size after the soaking step by any effective means, such as, chopping.

For the soak, the sea algae/halophyte and water are combined. The acid (concentrated or partially prediluted with water) can be added to the water before the sea algae/halophyte is introduced, or an acid aqueous solution can be used. Sufficient acid is used to form a dilute acid aqueous solution containing sea algae/halophyte. The term solution is used herein (though technically a dilute slurry may be a more correct term due to the insoluble sea algae/halophyte entities).

Sufficient acid is used to prepare a dilute acid aqueous solution (pH 5 or less) and advantageously acid is added as necessary during the soaking to maintain the dilute acid aqueous solution. The amount of acid used advantageously provides a pH of 2, to 4, and advantageously the amount of any later added acid is sufficient to maintain a pH in such range. The amount of acid used preferably provides a pH of 2.5 to 3.5, and preferably the amount of any later added acid is sufficient to maintain a pH in such range.

The inorganic acid can be a strong inorganic acid, such as, hydrochloric acid, nitric acid, sulfuric acid, hydrobromic acid, hydroiodic acid, perchloric acid, and chloric acid. A strong inorganic acid is an acid compound which ionizes completely or almost completely in aqueous solution. The inorganic acid can also be a weak inorganic acid, such as phosphoric acid and sulfurous acid.

Organic acids are considered to be strong organic acids if they have a $pK_a$ of less than 3.75. For each organic acid, a constant of dissociation ($pK_a$) is defined as the pH at which 50 percent of the organic acid is dissociated and 50 percent is non-dissociated. The organic acid can be a strong organic acid, such as, $CH_2ClCOOH$, $CHCl_2COOH$, $CCl_3COOH$, $CH_2FCOOH$, $CH_2BrCOOH$, $CH_2ICOOH$, $CH_3CH_2CHClCOOH$, $CF_3COOH$, HOOC-COOH, lactic acid, benzoic acid, and heptafluorobutyric acid. The organic acid can be a weak organic acid, such as, formic acid and acetic acid.

Non-aqueous solvents and other non-acid chemicals are normally not used or added to or during the soak.

The dilute acid soak of the sea algae/halophytes can be done in any type and size of suitable vessel. The vessels should be constructed of materials, e.g., stainless steel, wood, fiberglass, various plastics that are not corroded, or otherwise attacked by the acid or the sea algae/halophytes, before or after acid treatment, or that are separated from the sea algae/halophyte by the acid treatment.

The dilute acid soak can be conducted using a batch or continuous flow system. Either system can use two or more vessels where the aqueous solution is moved from vessel to vessel, respectively, on a batch basis or on a continuous flow basis.

The dilute acid soak is best done with slow agitation, such as, with rotating paddles, bubbles through the solution, pumps, etc., in particular in the batch schemes. The object is to create movement in the solution.

The soak can generally be conducted at any effective temperature above freezing and below boiling of the solution that achieves substantial reduction of the mineral content of the sea algae/halophyte. Advantageously, the soak is conducted at a temperature between 60 and 180° F., preferably 66 to 120° F. The reduction of the salt content is faster the higher the temperature, however the cost of using the higher temperature is an economic negative. The most preferred temperature for the soak is ambient temperature provided it is not so low as to cause too slow mineral removal, operational problems, and the like.

The soak is preferably conducted at ambient pressure, although higher and lower pressures can be used. When other than ambient pressure is used, sealed vessels are required.

After the acid treatment of the sea algae/halophyte, the sea algae/halophyte can be separated from the aqueous soak solution by any suitable separation technique, such as, filtration or centrifugation (e.g., basket-type centrifuge), or combinations of separation techniques. The aqueous soak solution can be allowed to set so that the solids therein settle, then most of the liquid containing the dissolved constituents can be removed by decanting, pumping, etc., and, if desired, the solids portion further dewatered, e.g., centrifugation, and/or dried. Nets or baskets are preferably used to keep the sea algae/halophyte in the solution and easily removable at the completion of the soaking phase.

The separated solids portion can be dried by any suitable manner, e.g., sun drying, heat dryers, etc.

Basically, the invention process uses and ends with the entire sea algae/halophyte (i.e., constituents) minus a substantial amount of the initial mineral content thereof.

The minimum time for the dilute acid soak is three hours to provide sufficient length of time to substantially reduce the salt content of the sea algae/halophyte. The soak time can be as long as necessary (although at least 3 hours) to achieve such result. While the soak time depends in part on the soak temperature, advantageously it is 5 to 12 hours and preferably 6 to 8 hours. Times as high as 20 hours, or more, can be used if necessary.

The separated acid-treated sea algae/halophyte has increased nutritional value compared to the initial sea algae/halophyte (since a substantial amount of the mineral content thereof has been removed).

The protein content of sea algae varies depending on the species, etc. The protein content is low in brown algae at 5 to 11 percent of dry matter, but comparable in quantitative terms to legumes at 30 to 40 percent of dry matter in some species of red algae. Green algae also have a significant protein content. Sea algae, depending on the species, etc., contain most of the vitamins. The main ones are provitamin A in the form of beta- and alpha-carotene found in red and brown algae, with contents of 2 to 17 mg/100 g dry; vitamin C in red and brown algae, with contents ranging from 50 to 300 mg/100 g dry; and vitamin E in brown algae. Most B-group vitamins are found in sea algae. Sea algae contains B12. The lipid content of seaweeds is very low, ranging from 1 to 5 percent of dry matter. Green algae have a much higher oleic (C 18:1) and alpha linoleic (w3-C18:3) acid content. Red algae have a high 20-carbon polyunsaturated fatty acid content, particularly the EPA (w30-C20:5). Arachidonic acid (w6-C20) is also well represented. They also contain 18-carbon polyunsaturated fatty acids (linolenic or linoleic). In brown algae, fatty acid distribution is fairly comparable, with a higher linolenic acid concentration. Seaweeds have a high total dietary fiber content (32 to 50 percent of dry matter). Among the insoluble fibers, there is a low percentage of cellulose, lignin and Floridean starch, particularly in red algae. (Insoluble fibers are usually associated with reducing passage times through the colon.) The soluble fiber fraction accounts for 51 to 56 percent of total fibers in green (ulvans) and red algae (agars, carrageenans and xylans) and for 67 to 87 (percent) in brown algae (laminarans, alginates and fucans). (Soluble fibers are generally associated with hydration performance, i.e., absorption, retention and swelling, which affect the food bolus's passage through the stomach and small intestine, and can have cholesterol-lowering and hypoglycaemic effects.)

The nutrient constituents, set out above for sea algae, of untreated sea algae/halophytes are significantly increased in the acid-treated sea algae/halophytes of the invention (due to the mineral reduction in the initial sea algae/halophytes by the invention process).

The acid treated sea algae/halophyte is more palatable and digestible than untreated sea algae/halophyte.

The acid treated sea algae/halophyte can be used as or in animal fodder or human food. For such use the acid-treated sea algae/halophyte is normally dried and ground. For example, the acid-treated sea algae/halophyte can be sold as a dry powder in health food stores. The acid-treated sea algae/halophyte can be mixed with other food or fodder ingredients.

According to the invention, a feed/food ingredient has been prepared (according to the invention) by reducing the ash (mineral) content of halophytic plants so they can be used as a substantial component of the diet. For example, sheep, goats and dairy cattle have been fed with a ration composed of up to 75 percent of various halophytic plant material, processed with acid soak according to the invention, with results comparable to rations containing the usual hay, corn and soybean or cottonseed meal. Also, the halophytic plant material (prepared according to the invention) was fed to monogastric animals (in a lower amount), and the animals ate it normally and it also contributed to excellent pigmentation to, for example, the red color of crustacea and the yellow color of egg yolk. This is a significant point because of the controversy over the use of "artificial" sources of pigmentation in animals and animal products to be consumed by humans.

The aqueous solution that results from the separation of the treated sea algae/halophyte from the aqueous solution (slurry) of acid and sea algae, contains the minerals removed from the sea algae by the acid soak. Dry sea algae/halophyte has a total mineral content of about 25 to about 40 weight percent. The acid soak reduces the mineral content of the sea algae to about 5 to about 15 weight percent, based on the dry weight of the acid-treated sea algae. The separate aqueous solution contains the amount of mineral removed from the sea algae/halophyte.

Sea algae contains a number of minerals, i.e., macronutrients such as sodium, calcium, magnesium, potassium, chlorine, sulfur and phosphorus, as well as trace elements essential for avoiding deficiencies, such as, iodine, iron, zinc, copper, selenium and molybdenum, and many other elements such as fluoride, manganese, boron, nickel and cobalt. Halophytes also contain a number of minerals. The aqueous solution, from which the acid-treated sea algae/halophyte has been separated, contains the minerals removed from the initial sea algae/halophyte. Such mineral-rich aqueous solution can be totally or partially dewatered and used as a source of minerals, particularly calcium, manganese and iodine.

There is a process for the production of alginates from sea algae that has pretreatment of the sea algae that includes treatment with dilute mineral acid for an hour or less. The process of the invention involves soaking sea algae/halophytes in a dilute aqueous solution of a mineral acid for at least three hours.

Truus, Kalle, et al., ibib., page 98, discloses that, before the dilute mineral acid pretreatment with hydrochloric acid, the sea algae is stored in weak $CaCl_2$ solution at room temperature for 18 hours. The invention process does not include pretreatment with storage in $CaCl_2$ solution or soaking in media that included $CaCl_2$. The reference also discloses that if alginate extraction is done with boiling water and treatment with weak $CaCl_2$ solution.

The Training Manual On *Gracilaria* Culture and Seaweed Processing In China, ibid., pages 12 and 13, discloses the preparation of alginate from sea algae using the calcification process. The first step in the manufacture of alginate is to convert the insoluble calcium and magnesium alginate into soluble sodium alginate by ion exchange under alkaline condition. In order to facilitate the ion exchange process the alginophyte can be treated with dilute mineral acid before alkali extraction. The longest time, located in the literature, for the dilute acid pretreatment was one hour. Before the dilute mineral acid pretreatment, the sea algae is treated with formalin solution to fix the pigments and the phenobic substance. (Formaldehyde has been applied in the industry to sea algae to preserve the sea algae, however the resultant formaldehyde residue is toxic.) The crude sodium alginate solution extracted is filtered and precipitated with $Ca^{2+}$ to form the insoluble calcium salt. The latter, upon separation, is converted to insoluble alginic acid by acidification for the removal of calcium ions. Then the alginic acid gels, after dehydration, are mixed with alkali ($Na_2CO_3$) powder to convert to soluble sodium salt again. Finally, the sodium alginate pastes formed are dried and milled to sodium alginate powder. The invention process of soaking sea algae in dilute acid aqueous solution differs from the acid pretreatment schemes in that, for example, the acid soak of the invention is much longer than such acid pretreatment stages (i.e., at least three hours versus one hour or less).

Also, the invention process does not use a base or formaldehyde before the dilute acid soak. The teaching of this invention process is that the minerals are maintained in an ionic state until separation of the sea algae/halophyte from the solution containing the dissolved minerals.

What is claimed is:

1. A process of treating sea algae and/or halophytes, comprising soaking the sea algae/halophytes in an aqueous solution containing a sufficient amount of acid to provide the aqueous solution with a pH of 2.0 to 4.0, for a sufficient length of time to substantially reduce mineral content of the sea algae/halophyte to about 5 to about 15 weight percent by dissolving mineral from said sea algae/halophyte, the mineral content of the sea algae/halophyte being expressed on the basis of the total ash content of the sea algae/halophyte in a dry state, and separating the treated sea algae/halophyte from the aqueous solution that contains the dissolved mineral removed from the sea algae/halophyte.

2. The process of claim 1, wherein the sea algae/halophyte is further dried.

3. The sea algae/halophyte of claim 1, wherein the sparated sea algae/halophyte is in wet state.

4. The process of claim 1, wherein the sea algae/halophyte is converted into smaller pieces after the soaking step.

5. The process of claim 1, wherein the sea algae/halophyte used in the soaking process has an initial total ash content of about 25 to about 40 weight percent, based on the initial dry weight of the sea algae.

6. The process of claim 1, wherein the soaking of the sea algae/halophyte is conducted for a minimum of 3 hours.

7. The process of claim 1, wherein the soaking of the sea algae/halophyte is conducted for 5 to 12 hours.

8. The process of claim 1, wherein the soaking of the sea algae/halophyte is conducted at ambient temperature.

9. The process of claim 1, wherein sufficient acid is present to provide a pH in the aqueous solution containing the sea algae/halophyte of 2.5 to 3.5.

10. The process of claim 1, wherein the acid is an inorganic acid.

11. The process of claim 1, wherein the acid is hydrochloric acid or sulfuric acid.

12. The process of claim 1, wherein the acid is an organic acid.

13. The process of claim 1, wherein the sea algae is a seaweed.

14. The process of claim 1, wherein the dissolved mineral is separated from the aqueous solution containing the dissolved mineral by drying or precipitation of the aqueous solution.

15. The process of claim 1, wherein the separated sea algae/halophyte is dried and reduced in size.

16. The sea algae/halophyte produced by the process of claim 1.

17. A process comprising utilizing the sea algae/halophyte prepared by the process of claim 15 as a food or feed ingredient.

18. A feed or fodder that includes the sea algae/halophyte prepared by the process of claim 1.

19. A process of treating sea algae and/or halophytes, comprising soaking the sea algae/halophytes in an aqueous solution containing a sufficient amount of acid to provide the aqueous solution with a pH of 2.0 to 4.0, for a minimum of 3 hours at 60° to 180° F. to substantially reduce mineral content of the sea algae/halophyte to about 5 to about 15 weight percent by dissolving mineral from said sea algae/halophyte, the mineral content of the sea algae/halophyte being expressed on the basis of the total ash content of the sea algae/halophyte in a dry state, and separating the treated sea algae/halophyte from the aqueous solution that contains the dissolved mineral removed from the sea algae/halophyte.

20. The process of claim 1, wherein the organic acid is formic acid, acetic acid or a strong organic acid.

* * * * *